United States Patent [19]

Malen et al.

[11] Patent Number: 4,766,114

[45] Date of Patent: Aug. 23, 1988

[54] TRICYCLIC COMPOUND CALLED 5-((3-CHLORO-6-METHYL-5,5-DIOXO-6,11-DIHYDRO-DIBENZO (C,F) (1,2)THIAZEPIN-11-YL)-AMINO) PENTANOIC ACID

[75] Inventors: Charles Malen, Fresnes; Jean C. Poignant, Bures S/Yvette, both of France

[73] Assignee: ADIR Et Compagnie, Neuilly-sur-Seine, France

[21] Appl. No.: 17,237

[22] Filed: Feb. 20, 1987

[30] Foreign Application Priority Data

Feb. 21, 1986 [FR] France ................................ 86 02399

[51] Int. Cl.[4] ..................... A61K 31/55; C07D 281/02
[52] U.S. Cl. ..................................... 514/211; 540/549
[58] Field of Search ......................... 540/549; 514/211

[56] References Cited

U.S. PATENT DOCUMENTS

3,821,249  6/1974  Malen et al. ........................ 540/549

FOREIGN PATENT DOCUMENTS

2065635  10/1979  Fed. Rep. of Germany ...... 514/211

OTHER PUBLICATIONS

Chemical Abstracts, vol. 82, (1975), Item 4333b, abstracting German Offenlegunsschrift 2,065,635, 5 Sep. (1974).

*Primary Examiner*—Robert T. Bond
*Attorney, Agent, or Firm*—Gordon W. Hueschen

[57] ABSTRACT

The invention concerns 5-[(3-chloro-6-methyl-5,5-dioxo-6,11-dihydro-dibenzo (c,f) (1,2) thiazepin-11-yl)-amino] pentanoic acid.

Medicament.

7 Claims, No Drawings

TRICYCLIC COMPOUND CALLED 5-((3-CHLORO-6-METHYL-5,5-DIOXO-6,11-DIHYDRO-DIBENZO (C,F) (1,2)THIAZEPIN-11-YL)-AMINO) PENTANOIC ACID

The present invention concerns a new tricyclic compound, the 5-[(2-chloro-6-methyl-5,5-dioxo-6,11-dihydro-dibenzo-(c,f)(1,2)thiazepin-11-yl)-amino]pentanoic acid, a process for the preparation thereof, and pharmaceutical compositions containing it.

Some tricyclic acids derived from (6-methyl-5,5-dioxo-6,11-dihydro-dibenzo(c,f)(1,2)thiazepin-11-yl)amine with interesting pharmacological properties were described in French Pat. No. 71.32197. Among these products, 7-[(3-chloro-6-methyl-5,5-dioxo-6,11-dihydro-dibenzo(c,f)(1,2)thiazepin-11-yl)amino]heptanoic acid was shown to have antidepressant properties and is therefore used in the treatment of depression.

Taking into account the very useful therapeutic results obtained with this product, further investigations have been carried out into this same chemical series and have led to the discovery of 5-[(2-chloro-6-methyl-5,5-dioxo-6,11-dihydrobenzo(c,f)(1,2)thiazepin-11-yl)-amino]pentanoic acid, which forms the object of the present invention. This compound has an original antidepressant profile with a much greater activity than the products described in the above-mentioned patent.

The present invention relates more especially to 5-[(3-chloro-6-methyl-5,5-dioxo-6,11-dihydro-dibenzo(c,f)(1,2)thiazepin-11-yl)-amino]pentanoic acid, which has the following chemical formula (I):

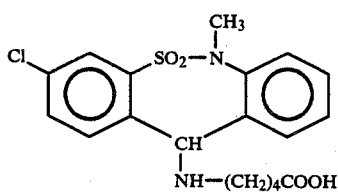

This compound has an asymmetrical carbon atom and therefore exists in the form of optical isomers which as such form part of the invention.

The new compound of formula I is an amphoteric compound yielding addition salts with pharmaceutically acceptable organic and mineral bases, and with organic or mineral acids. All these salts are included in the present invention. Among the bases used to obtain these salts, there may be mentioned sodium, potassium and calcium hydroxides, sodium carbonates and bicarbonates, and among the acids used, phosphoric, hydrochloric, sulphuric, acetic, propionic, citric, oxalic, benzoic acids etc.

The present invention also relates to a process for the preparation of the compound of formula I, which comprises condensing a halogenated derivative of the general formula II

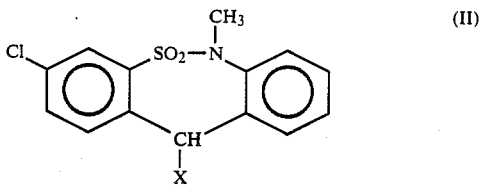

in which X represents a chlorine or bromine atom, with an ester of 6-amino pentanoic acid of the general formula III

$NH_2-(CH_2)_4COOR$ (III)

in which R represents a lower alkyl radical containing 1 to 4 carbon atoms, in base form of as one of its addition salts with a mineral or organic acid, and then saponifying the tricyclic ester so obtained to yield the derivative of the general formula I.

The condensation of compounds II and III is carried out in a suitable organic solvent such as nitromethane, in the presence of an acceptor of the hydracid formed during the reaction and at a temperature of between 20° and 100° C.

The saponification of the tricyclic acid so obtained is carried out in an alkaline aqueous alcoholic solution.

The halogenated derivatives of the general formula II are described in French Pat. No. 1.566.191.

The compound of the formula I has a much greater antidepressant activity than 7-[(3-chloro-6-methyl-5,5-dioxo-6,11-dihydro-dibenzo(c,f)(1,2)thiazepin-11-yl)-amino]heptanoic acid which is the most active compound among those described in French Pat. No. 71.32197.

The standard pharmacological tests used to evaluate the antidepressant activity of new chemical compounds, described, in particular, in Enna S. J. et al. "Antidepressants: Neurochemical Behavioral, and Clinical Perspectives" Raven Press N.Y. 1981, p. 107–120 showed that 5-[(3-chloro-6-methyl-5,5-dioxo-6,11-dihydrodibenzo(c,f)(1,2)thiazepin-11-yl)-amino]pentanoic acid has a very potent antidepressant activity.

The pharmacological properties of the compound of the invention therefore enable it to be used in the treatment of depression.

The invention also includes pharmaceutical compositions containing the formula I compound, one of its optical isomers or one of its addition salts formed with a pharmaceutically compatible base or acid, as active principle, in association with one or several inert and non-toxic excipients.

The pharmaceutical compositions so obtained are advantageously presented in various forms such as, for example, tablets, sugar coated tablets, capsules, glossettes or other pharmaceutical preparations suitable for sublingual administration, suppositories, solutions for injection or oral administration.

The pharmaceutical compositions included in the invention may also contain another active principle with a complementary or synergic action.

The dose may vary widely as a function of the age or weight of the patient, but in particular according to the route of administration and the severity of the disorder.

The preferred route of administration is the oral or parenteral route. In general, the unit dosage will range from 1 to 10 mg and the daily dosage from 1 to 50 mg.

The following non-limitative examples, illustrate the invention.

EXAMPLE 1

5-[(3-chloro-6-methyl-5,5-dioxo-6,11-dihydro-dibenzo(c,f)(1,2)thiazepin-11-yl)-amino]pentanoic acid Stage A:

Ethyl 5-[(3-chloro-6-methyl-5,5-dioxo-6,11-dihydrodibenzo(c,f)(1,2)thiazepin-11-yl)-amino]pentanoate.

0.072M of 3,11-dichloro-6-methyl-5,5-dioxo-6,11-dihydrobenzo(c,f)(1,2)thiazepin are heated with 0.072M of ethyl 5-amino pentanoate hydrochloride in 215 ml of previously dried nitromethane for 2 hours at 60° C., while stirring and in the presence of 0.144M triethylamine.

After evaporation of the solvent under reduced pressure, the residue is taken up in ether and water. The two solvents are separated and the organic phase is washed with water and then dried over anhydrous sodium sulphate. After evaporation of the organic solvent, ethyl 5-[(3-chloro-6-methyl-5,5-dioxo-6,11-dihydro-dibenzo(c,f)(1,2)thiazepin-11-yl)-amino]pentanoate is obtained in the form of an oily residue.

Yield 82%.

The infrared spectrum of this compound, recorded in a 1 mm sodium chloride cell, presents a fine band at 3,400 cm$^{-1}$, characteristic of the amine group, and a band at 1,720 cm$^{-1}$, corresponding to the valence vibration of the ester group carbonyl.

Stage B:

5-[(3-chloro-6-methyl-5,5-dioxo-6,11-dihydro-dibenzo(c,f)(1,2)thiazepin-11-yl)-amino]pentanoic acid 0.039M of the product obtained during the previous phase are dissolved in an aqueous alcoholic mixture containing 39 ml of N sodium hydroxide and 80 ml of ethanol. The solution is left to stand for 12 hours at ambient temperature and then the ethanol is evaporated under a vacuum. The residue is distributed between the water and ether.

After adding a sufficient quantity of N hydrochloric acid to slightly acidify the aqueous phase (pH=6.3), an oily precipitate is formed. This oil is extracted with dichloromethane. The organic solution obtained in this way is washed with water and then dried over anhydrous sodium sulphate. After elimination of the solvent under a vacuum, the residue is taken up in 100 ml of acetonitrile, and the solution is cooled to 0° C. The precipitate formed is isolated by filtration and then recrystallized in 180 ml of acetonitrile. 0.020M 5-[(3-chloro-6-methyl-5,5-dioxo-6,11-dihydro-dibenzo(c,f)(1,2)thiazepin-11-yl)-amino]pentanoic acid is obtained.

Yield 49%.

| Elementary analysis: ($C_{19}H_{21}ClN_2O_4S$) | | | | |
|---|---|---|---|---|
| C | H | N | Cl | S |
| % found 55.69 | 5.21 | 6.75 | 8.68 | 7.93 |
| % calculated 55.80 | 5.17 | 6.85 | 8.67 | 7.84 |

Proton nuclear magnetic resonance spectrum recorded at 60 MHz in solution in a $CDCl_3$-D.M.S.O. mixture.

1.6 ppm, m, 4H; 2.1 to 2.70 ppm, m, 4H; 3.4 ppm, s, 3H; 4.5 ppm, 2 exchangeable protons, 5.0 ppm, s, 1H; 7.2 to 8.0 ppm, m, 7H.

Mass spectrum (Chemical ionization, $NH_3$, 0.3 Torr).

409 m/z [M+1]$^+$ (100%); 391 m/z (3%); 311 m/z (19.3%); 294 m/z (4.2%); 292 m/z (21.1%); 232 m/z (9.6%); 230 m/z (10.2%); 118 m/z (9.9%).

PHARMCOLOGICAL STUDY

The antidepressant activity of the formula I compound was evaluated using different in vivo tests and compared to that of 7-[(3-chloro-6-methyl-5,5-dioxo-6,11-dihydro-dibenzo(c,f)(1,2)thiazepin-11-yl)-amino]-heptanoic acid (TAHA).

EXAMPLE 2

Effects on reserpine-induced ptosis in the mouse

This experiment was carried out on groups of 20 male NMRI mice (IFFA-CREDO), with an average weight of 20±2 g. The compound of the formula I and TAHA, at the dose of 25 mg.kg$^{-1}$, or water for injections, were given intraperitoneally, 1 hour after the intravenous injection of a dose of 2 mg.kg$^{-1}$ of reserpine, according to the method described by C. GOURET et al., in J. Pharmacol., 1977, 8, (3) p. 333-350.

One hour after the injection of the reserpine, the animals were placed on a 5 cm×5 cm square, wood platform for 20 seconds. Ptosis was considered to be positive if the animal's eyes remained shut during the 20 seconds after it was placed on the platform. On the other hand, the animal was considered to be protected if the eyes were not completely closed during the 20 seconds following the moment when it was placed on the platform.

TAHA, at the dose of 25 mg.kg$^{-1}$ IP, slightly antagonised the ptosis induced by the IV injection of 2 mg.kg$^{-1}$ reserpine as only 32% of the animals were protected. The compound of the formula I, at the same dose, was much more active and protected 53% of the animals.

EXAMPLE 3

Effects on reserpine-induced hypothermia in the mouse

This study was carried out on experimental groups of 10 NMRI mice (IFFA-CREDO) fasted for 18 hours. The "test" groups of mice were treated by the intraperitoneal injection of 50 mg.kg$^{-1}$ of TAHA or compound of the formula I. The "control" group was given the same volume of isotonic saline solution. One hour later, all the animals were given an intraperitoneal injection of 2 mg.kg$^{-1}$ of reserpine. Hypothermia was evaluated 4 hours after the injection of reserpine by measuring the rectal temperature using an electric thermometer.

As shown by table I, the two products antagonised the hypothermia induced by reserpine. For TAHA, this antagonism led to a 10% increase in temperature in comparison with the control group. The antagonist activity of compound of the formula I was much higher as the dose of 50 mg.kg$^{-1}$ IP, produced an increase in the temperature of approximately 25%.

TABLE I

| IP TREATMENT | FINAL TEMPERATURES | |
|---|---|---|
| | MEAN ± SD | % CHANGE |
| CONTROLS WATER + 2 mg · kg$^{-1}$ reserpine | 24.7 ± 0.88 | |
| 50 mg · kg$^{-1}$ TAHA + 2 mg · kg$^{-1}$ reserpine | 27.1 ± 1.40 | +10% |
| 50 mg · kg$^{-1}$ compound of the formula I + | 30.9 ± 3.7 | +25% |

TABLE I-continued

| IP TREATMENT | FINAL TEMPERATURES | |
|---|---|---|
| | MEAN ± SD | % CHANGE |
| 2 mg · kg$^{-1}$ reserpine | | |

SD = Standard Deviation

EXAMPLE 3

Effects on tetrabenazine-induced ptosis in the mouse

Male CD mice (Charles River), of average weight 23 g, were distributed in groups of 12 animals. Compound of the formula I, TAHA or water for injections (controls) were given intraperitoneally, 15 minutes after the injection of 20 mg.kg$^{-1}$ of tetrabenazine by the same route. The dose of products tested was 25 mg.kg$^{-1}$. The animals were observed individually 5, 25, 35 and 55 minutes after the injection of the tetrabenazine and the intensity of the ptosis was evaluated using a 0 to 4 rating scale.

As shown by the results given in Table II, at the dose of 25 mg.kg$^{-1}$, the compound of the formula I had a much greater and long-lasting activity than TAHA.

TABLE II

| TREAT-MENT | MEAN VALUE OF THE PTOSIS INTENSITY SCORE ± SD | | | |
|---|---|---|---|---|
| | 5 MINUTES | 25 MINUTES | 35 MINUTES | 55 MINUTES |
| Controls m | 1.33 ± 0.65 | 2.58 ± 0.51 | 2.83 ± 0.58 | 3.08 ± 0.51 |
| Form. I Compound m | 0.42 ± 0.51 | 1.75 ± 0.45 | 1.83 ± 0.39 | 2.42 ± 0.67 |
| % controls | −69 | −32 | −35 | −22 |
| TAHA + tetra- benazine m | 0.50 ± 0.52 | 1.92 ± 0.51 | 2.25 ± 0.45 | 2.58 ± 0.51 |
| % controls | −62.5 | −26 | −21 | NS | m = mean of the scores observed
% controls = % change of the total number of mean scores in comparison with the controls
NS = Non significant
SD = Standard Deviation

EXAMPLE 5

Effects on the aggressivity of isolated mice

The male CD mice (Charles RIVER) used in this study were housed in small (18×10×10 cm) individual cages with the walls painted black, with one mouse per cage, for several months, at a constant temperature of 21° C. and in a light-darkness cycle of 12 hours. The average weight of the mice at the time of the study was 45 g.

Each experimental group comprised 10 couples of mice previously selected for their aggressivity. The aggressivity test was carried out on non-fasting animals. The "intruding" mouse of each couple was placed in the cage containing the other mouse for a 3 minute period. For each experimental group of 10 couples, the percentage of protected couples, that is those which did not attack each other during the three minute test period, was noted.

In the present test, doses of 10 and 20 mg.kg$^{-1}$ of TAHA and the compound of the formula I were used. The product was administered by the intraperitoneal route, 30 minutes before the test.

As shown in table III, only the dose of 20 mg.kg$^{-1}$ IP of TAHA or the compound of the formula I had a clear anti-aggressive effect in this test with the protection of 40% and 60% of the couples respectively (0% in the control group). The letter S in the table represents statistically significant changes.

The anti-aggressive activity of the compound of the formula I was much greater than that of TAHA in this model.

TABLE III

| TREATMENT | MEAN NUMBER OF ATTACKS ± SD | % OF PROTECTED COUPLES (no attack) |
|---|---|---|
| Controls Water | 6.7 ± 4.7 | 10% |
| ATAH 10 mg · kg$^{-1}$ | 7.2 ± 4.6 | 10% |
| Controls water | 5.4 ± 2.8 | 10% |
| Compound of the formula I 10 mg · kg$^{-1}$ | 7.2 ± 5.9 | 20% |
| Controls water | 8.3 ± 6.0 | 0% |
| ATAH 20 mg · kg$^{-1}$ | 3.7 ± 4.9 | 40% S |
| Compound of the formula I 20 mg · kg$^{-1}$ | 3.9 ± 6.2 | 60% S |

SD = Standard Deviation

PHARMACEUTICAL PREPARATION

EXAMPLE 6

Capsules containing 0.005 g of 5-[(3-chloro-6-methyl-5,5-dioxo-6,11-dihydro-dibenzo(c,f)(1,2)thiazepin-11-yl)-amino]pentanoic acid

| | |
|---|---|
| 5-[(3-chloro-6-methyl-5,5-dioxo-6,11-dihydro-dibenzo (c,f) (1,2) thiazepin-11-yl)-amino] pentanoic acid | 0.0050 g |
| Maize starch | 0.0320 g |
| Microcrystalline cellulose | 0.0262 g |
| Lactose | 0.0720 g |
| Colloidal silica | 0.0030 g |
| Magnesium stearate | 0.0015 g |
| Talc | 0.0030 g |
| For a white, N° 3 capsule | |

We claim:

1. Compound of the formula I

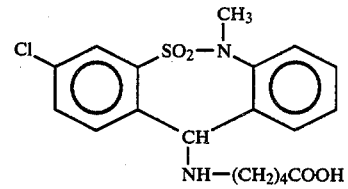

(I)

in its racemic form or optical isomers or addition salts thereof with a pharmaceutically acceptable organic or mineral base or mineral or organic acid.

2. Pharmaceutical composition useful in treating depression containing an antidepressive amount of the compound according to claim 1 as active principle, in association or in admixture with a pharmaceutically-acceptable, non toxic, inert excipient or vehicle.

3. Pharmaceutical composition according to claim 2 containing the active principle at the dose of 1 to 10 mg.

4. A method of treating depression comprising the step of administering to a subject suffering from depression an antidepressive amount of a compound of claim 1.

5. A method of claim 4 wherein the amount is between about one and ten mg per dose.

6. A method of treating depression comprising the step of administering to a subject suffering from depression an antidepressive amount of a composition of claim 2.

7. The method of claim 6 wherein the amount of the antidepressive compound in the composition is between about one and ten mg per dose.

* * * * *

UNITED STATES PATENT AND TRADEMARK OFFICE
CERTIFICATE OF CORRECTION

PATENT NO. : 4,766,114
DATED : August 23, 1988
INVENTOR(S) : Charles Malen and Jean C. Poignant It is certified that error appears in the above-identified patent and that said Letters Patent is hereby corrected as shown below:

```
Col. 1, lines 10 & 27; "5-[(2-chloro-" should read
  -- 5-[(3-chloro- --    (both occurrences)

Col. 4, line 5; "PHARMCOLOGICAL" should read
  -- PHARMACOLOGICAL --

Col. 5, line 9; "EXAMPLE 3" should read -- EXAMPLE 4 --
```

Signed and Sealed this

Third Day of January, 1989

Attest:

DONALD J. QUIGG

Attesting Officer

Commissioner of Patents and Trademarks